US009027550B2

(12) United States Patent
Lemper et al.

(10) Patent No.: US 9,027,550 B2
(45) Date of Patent: May 12, 2015

(54) PLATELET RICH PLASMA/STEM CELL DISPENSING SYSTEM AND METHODS THEREOF

(76) Inventors: Brian Lemper, Las Vegas, NV (US); Paul Regen, Felton, CA (US)

(*) Notice: Subject to any disclaimer, the term of this patent is extended or adjusted under 35 U.S.C. 154(b) by 0 days.

(21) Appl. No.: 13/618,555

(22) Filed: Sep. 14, 2012
(Under 37 CFR 1.47)

(65) Prior Publication Data

US 2013/0273008 A1 Oct. 17, 2013

Related U.S. Application Data

(60) Provisional application No. 61/534,848, filed on Sep. 14, 2011.

(51) Int. Cl.
| | |
|---|---|
| *A61M 16/14* | (2006.01) |
| *A61M 15/00* | (2006.01) |
| *A61M 11/00* | (2006.01) |
| *A61K 35/14* | (2006.01) |
| *A61M 16/06* | (2006.01) |
| *A61M 11/06* | (2006.01) |
| *A61M 16/00* | (2006.01) |
| *A61M 16/10* | (2006.01) |
| *A61M 16/20* | (2006.01) |

(52) U.S. Cl.
CPC ................ *A61K 35/14* (2013.01); *A61M 16/06* (2013.01); *A61M 16/14* (2013.01); *A61M 11/005* (2013.01); *A61M 11/06* (2013.01); *A61M 15/00* (2013.01); *A61M 16/0045* (2013.01); *A61M 16/1055* (2013.01); *A61M 16/208* (2013.01); *A61M 2202/0208* (2013.01); *A61M 2202/0415* (2013.01); *A61M 16/0093* (2014.02); *A61M 16/1065* (2014.02)

(58) Field of Classification Search
CPC ..... A61M 11/00; A61M 15/00; A61M 16/00; A61M 16/0045; A61M 16/0078; A61M 16/01; A61M 16/10; A61M 16/14
USPC .......................... 128/200.11–200.23, 200.24, 128/203.12–204.14, 203.28, 204.18
See application file for complete search history.

(56) References Cited

U.S. PATENT DOCUMENTS

| | | | | |
|---|---|---|---|---|
| 5,752,502 | A * | 5/1998 | King | 128/200.18 |
| 7,418,962 | B1 * | 9/2008 | Rao | 128/200.24 |
| 2007/0102280 | A1 * | 5/2007 | Hunter et al. | 204/157.15 |
| 2008/0283048 | A1 * | 11/2008 | Petersen | 128/200.14 |
| 2010/0112081 | A1 * | 5/2010 | Mishra et al. | 424/530 |
| 2010/0132706 | A1 * | 6/2010 | Nashed | 128/203.28 |
| 2012/0087988 | A1 * | 4/2012 | Gold | 424/530 |

* cited by examiner

*Primary Examiner* — Valerie L Skorupa
(74) *Attorney, Agent, or Firm* — Donald R. Boys; Central Coast Patent Agency, Inc.

(57) ABSTRACT

A method and apparatus is provided to separate Platelet Rich Plasma (PRP) utilizing standard whole blood harvesting techniques and separating the solution via centrifugation preparation. A pump is provided to pump PRP/Stem Cell solution from a centrifugation reservoir in to a nebulizer to aerosolize the PRP/Stem Cell solution in the nebulizer with oxygen. A patient will then inhale the aerosolized or vaporized PRP/Stem Cell solution into their respiratory system. Removal of any waste PRP/Stem Cell solution is provided by trapping the PRP/Stem Cells and any other biological matter other in a HEPA filter and allowing exhaled gasses to safely exit the from the Semi-Rebreathing Chamber.

4 Claims, 7 Drawing Sheets

PLATELET RICH PLASMA/STEM CELL DISPENSING SYSTEM AND METHODS THEREOF

CROSS-REFERENCE TO RELATED DOCUMENTS

The present invention is a Non-Provisional application of U.S. Provisional application 61/534,848, filed on Sep. 14, 2011. The disclosure of priority application is incorporated herein at least by reference.

BACKGROUND OF THE INVENTION

1. Field of the Invention

The present invention is in the field of cardiorespiratory therapy, and pertains more particularly to a device and a method of regenerative medicine, which employs the aerosolized delivery of an activated Platelet Rich Plasma/Stem Cell (PRP) solution to a patient's upper and lower respiratory system.

2. Discussion of the State of the Art

In the field of healthcare, specialists work with patients who are experiencing cardiopulmonary dysfunction. Respiratory therapy contains a broad range of specialty areas. Asthma, Pulmonary Fibrosis and Chronic Obstructive Pulmonary Disease (COPD) are just a few of the specialty areas within this field.

Recent case study trials suggest an improvement with pulmonary vascular oxygen exchange, in turn, reducing overall cardiorespiratory workload.

It is postulated on and in-vivo cellular level that activated-Platelet Rich Plasma/Stem Cell [{which has been shown to increase Vascular Endothelial Growth Factor (VEGF) as well as Platelet Derived Growth Factor (PDGF)-BB, Transforming Growth Factor beta (TGF-beta) and finally showed to have delayed release of Interleukin-1 beta (IL-1-beta) in vitro}-Clinical Oral Implants Research Oct. 18, 2007 studies performed by Roussey Y, Bertrand Dechesne M P, Gagnon G.] increases these growth factors in human tissues to genetically stimulate revascularization as well as improve alveolar membrane surface integrity, facilitating oxygen extraction and gaseous exchange of carbon dioxide. (i.e. diminishing pulmonary dead space, decreases the body's cardiorespiratory workload in order to easily maintain an acid base balance)

It is also postulated that by decreasing chronic pulmonary vascular inflammation we will cause a decrease in the overall cardiopulmonary vascular sympathetic tone-possibly leading to a non-pharmacologic maintenance therapy for reactive airway disease.

Motivation for these studies came about while observing the failure of steroid therapy to control most cardiorespiratory disease processes long-term. With a culture of ever growing acceptance of pharmacologic side effects, we found it necessary to challenge conventional anti-inflammatory/steroid therapy treatments for chronic morbidities.

Since World War I it has been understood that activated blood provides a "super charge" to damaged or dying tissues. We have since studied and have obtained a better understanding of the powers of undifferentiated white blood cells within our normal circulating blood volume. As Americans, we have been exposed to Stem Cell Research and breakthrough technologies for decades now. What we at American Regenerative Technologies (ART, LLC) are proposing is to utilize adult autologous stem cells (self) to not only assuage the fear that the use of embryonic stem cells theoretically could manipulates the genome, as well as to provide a patient centric understanding of how to augment naturally occurring healing processes.

The utilization of a combination of autologous-Hematopoietic Stem Cell in activated-Platelet Rich Plasma/Stem Cell is simply analogous to sending an architect and a carpenter into a broken structure with all the tools, workers and supplies necessary to complete a building rehab project.

The nebulized/aerosolized delivery system for Platelet Rich Plasma/Stem Cell was logically derived by modifying standard breathing circuit with state-of-the-art therapeutic concepts for safe, minimally invasive revitalization of damaged human pulmonary, vascular and neurologic tissue.

SUMMARY OF THE INVENTION

It occurred to the present inventors in an inventive moment that a new, simpler and less toxic invention was needed in this field. Such an invention will separate Platelet Rich Plasma (PRP) utilizing standard whole blood harvesting techniques and separating via centrifugation preparation. Such an invention will pump the separated PRP/Stem Cell solution from the centrifugation reservoir in to a nebulizer. Such an invention will aerosolize the PRP/Stem Cell solution in the nebulizer with oxygen. Such an invention will allow a patient receiving respiratory therapy to inhale the aerosolized or vaporized PRP/Stem Cell solution into their respiratory system. Such an invention will capture any unused portion of the aerosolized PRP/Stem Cell solution, which the patient expels within a Semi-Rebreathing Chamber. Such an invention will recycle any unused portion of the aerosolized PRP/Stem Cell solution, captured within the Semi-Rebreathing Chamber back into the patient's respiratory system. Such an invention will remove any waste PRP/Stem Cell solution trapping the PRP/Stem Cells and any other biological matter other in a HEPA filter and allowing exhaled gasses to safely exit the from the Semi-Rebreathing Chamber. Such an invention will filter any exhaust through a disposable filter. Such an invention will sterilize any exhaust with ultraviolet radiation before it exits the system. Such an invention will contain a display for viewing information about the patient's respiratory therapy. Such an invention will contain controls for making adjustments to the patient's respiratory therapy. In various embodiments of the present invention different features may be combined and in some cases omitted without changing the scope of the invention. For example in one embodiment a Semi-Rebreathing Chamber is omitted and in other embodiments it is included (or) in some embodiments an Ultraviolet Light is present for the purpose of sterilizing biological matter and in other embodiments it is not present.

It will be apparent to the skilled artisan that there are a broad variety of changes that may be made in the embodiments of the invention described below without departing from the spirit or scope of the invention. For example, the Transfer Tubing, Oxygen Line and Nebulizer Power Cord may be combined together to produce a single component, similar to how the Transfer Tubing and Oxygen Line were combined in the figures shown. Furthermore, the entire system is, as well, designed to function with stem cells or other combinations of regenerative solutions or any other immune system enhancing solution.

BRIEF DESCRIPTION OF THE DRAWING FIGURES

FIG. 1 is an illustration of a Platelet Rich Plasma/Stem Cell Dispensing System, containing an Automatic Centrifuge/PRP Processing System, according to an embodiment of the present invention.

Figure 1:
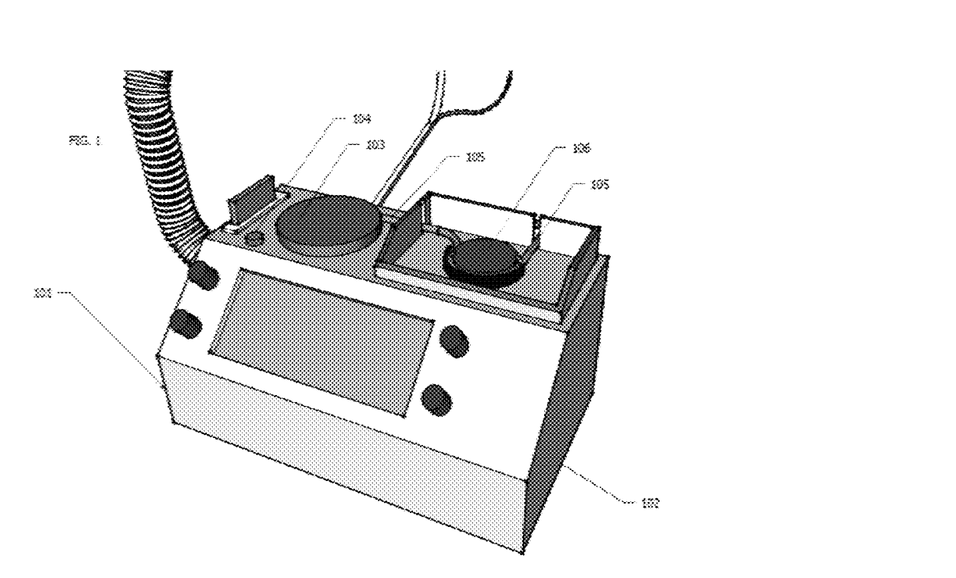
Figure 2:
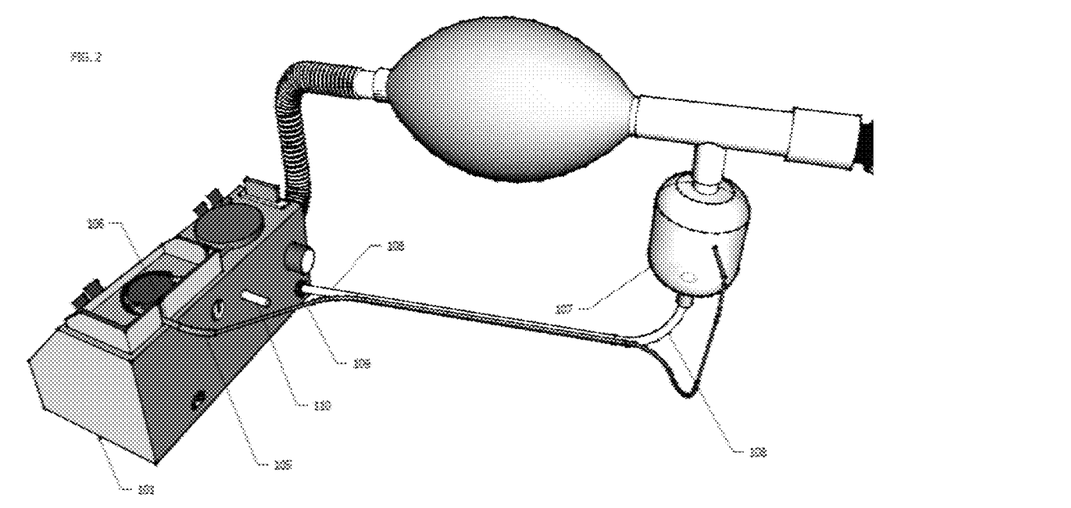
FIG. 2 is a rear-view illustration of a Platelet Rich Plasma/Stem Cell Dispensing System.
Figure 3:
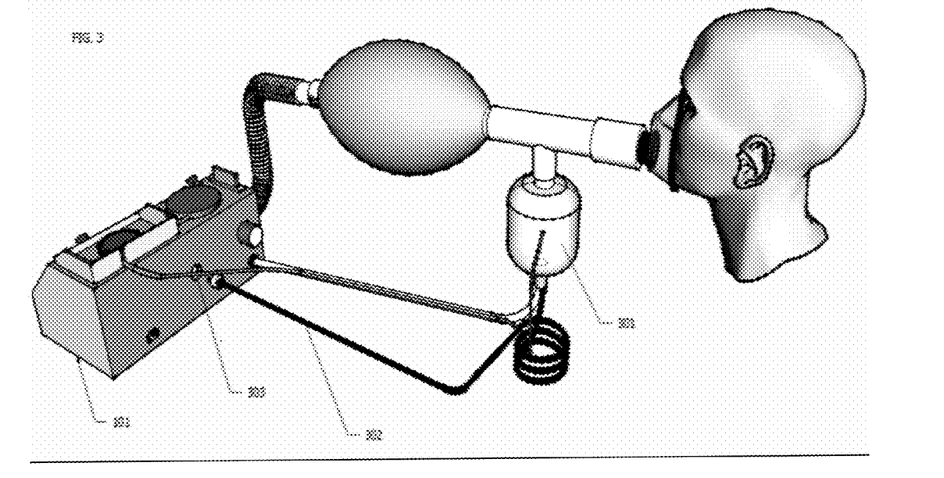
FIG. 3 is a rear-view illustration of a Platelet Rich Plasma/Stem Cell Dispensing System, detailing the Nebulizer and its components.
Figure 4:
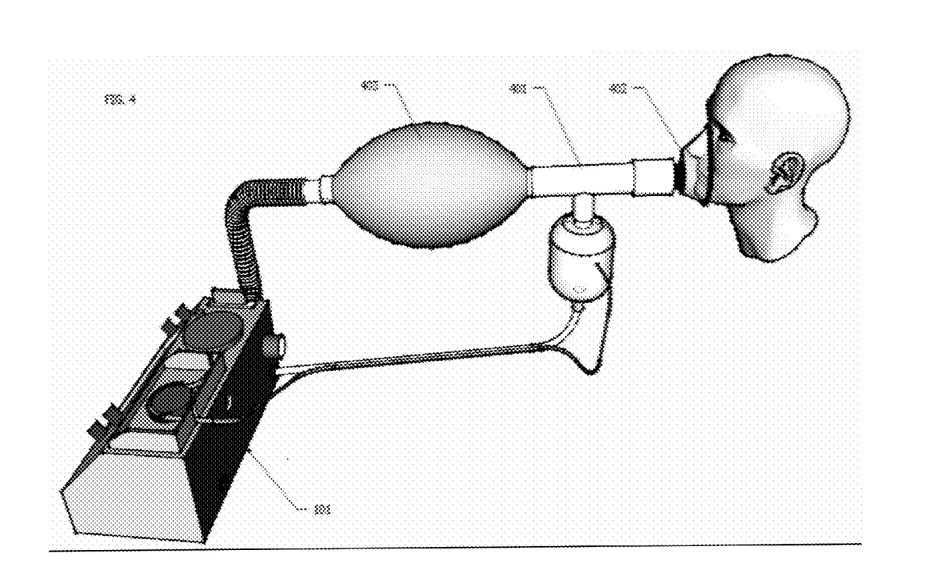
FIG. 4 is a side-view illustration of a Platelet Rich Plasma/Stem Cell Dispensing System, detailing the Connector, Face Mask and Semi-Rebreathing Chamber.

| | Element Number | Element Name |
|---|---|---|
| FIG. 4 | 101 | Platelet Rich Plasma/Stem Cell Dispensing System |
| | 401 | Connector |
| | 402 | Face Mask |
| | 403 | Semi-Rebreathing Chamber |

FIG. 4 is a side-view illustration of a Platelet Rich Plasma/Stem Cell Dispensing System 101, detailing the Connector, Face Mask and Semi-Rebreathing Chamber, according to the embodiment of the present invention. In another embodiment, the Platelet Rich Plasma/Stem Cell Dispensing System may also contain Connector 401. In one embodiment, the Connector may be attached to the top of the Air-Flow Driven Nebulizer containing the Platelet Rich Plasma/Stem Cell solution.

In one embodiment, one end of the Connector may be connected to the end of Face Mask 402. In one embodiment, the Face Mask may be placed over the nose and mouth of the patient receiving respiratory therapy. In this embodiment, the patient may breathe normally to inhale the Platelet Rich Plasma/Stem Cell solution into their respiratory system.

In another embodiment, the Face Mask may contain a Head Strap. In one embodiment, the Head Strap may be placed behind the patient's head to secure the Face Mask over the patient's nose and mouth. In this embodiment, the Head Strap may allow the patient to receive hands free respiratory therapy (patient will have their hands free to do other things while receiving therapy).

In one embodiment, the opposite end of the Connector (the end opposite to the Face Mask) may be connected to Semi-Rebreathing Chamber 403. In one embodiment, any unused portion of the aerosolized Platelet Rich Plasma/Stem Cell solution which is expelled from the patient's respiratory system may become contained within the Semi-Rebreathing Chamber. In this embodiment, the unused portion of the aerosolized Platelet Rich Plasma/Stem Cell solution may be recycled back into the patient's respiratory system.

Figure 5:
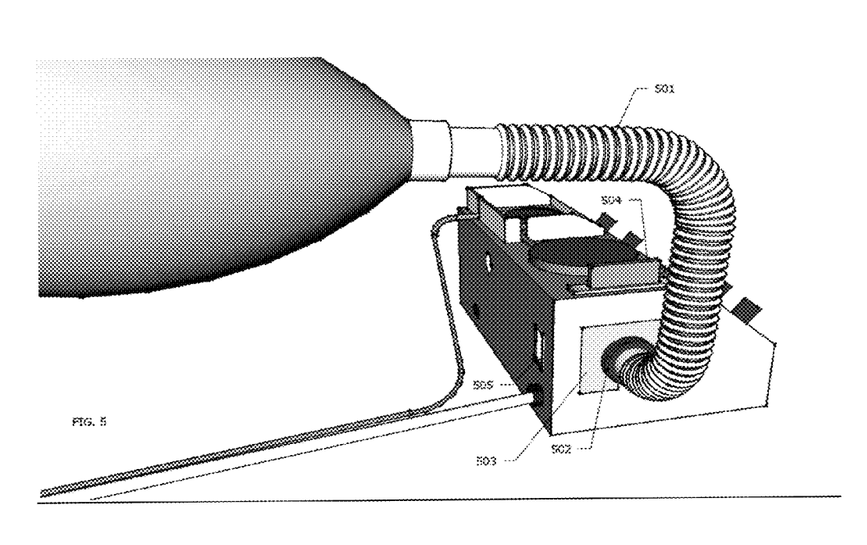
FIG. 5 is a side-view illustration of a Platelet Rich Plasma/Stem Cell Dispensing System, detailing Exhaust System.
Figure 6:
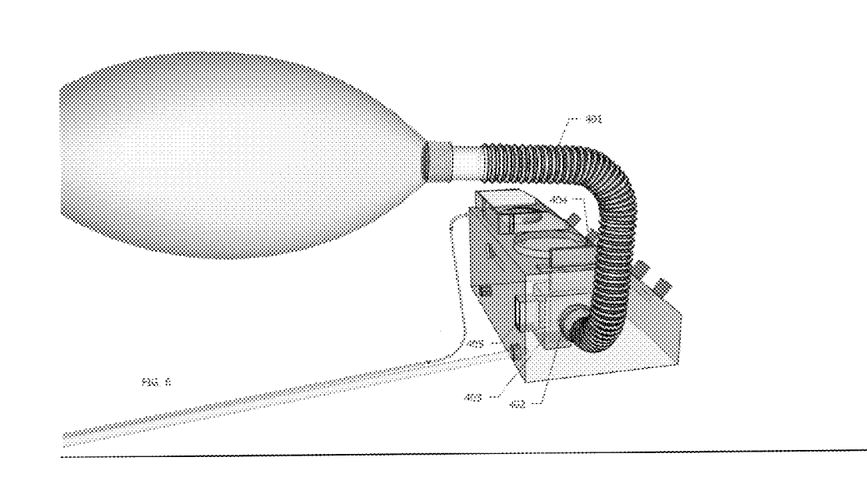
FIG. 6 is an x-ray view of a Platelet Rich Plasma/Stem Cell Dispensing System, detailing Exhaust System and internal components.

| | Element Number | Element Name |
|---|---|---|
| FIG. 5 | 101 | Platelet Rich Plasma/Stem Cell Dispensing System |
| | 501 | Corrugated Exhaust Tubing |
| | 502 | Disposable Positive End Expiratory Pressure Valve |
| | 503 | Intake Port |
| | 504 | Disposable HEPA Filter |
| | 505 | Exhaust Port |

FIG. 5 is a side-view illustration of a Platelet Rich Plasma/Stem Cell Dispensing System 101, detailing Exhaust System, according to the embodiment of the present invention. In another embodiment, the Platelet Rich Plasma/Stem Cell Dispensing System may also contain Corrugated Exhaust Tubing 501, which may be attached to the Semi-Rebreathing Chamber. In this embodiment, Corrugated Exhaust Tubing may remove any waste, aerosolized Platelet Rich Plasma/Stem Cell solution (which is not recycled into the patient's respiratory system at the Semi-Rebreathing Chamber stage); and any Carbon Dioxide which the patient expels.

In another embodiment, the Platelet Rich Plasma/Stem Cell Dispensing System may also contain Disposable Positive End Expiratory Pressure Valve 502, (also known as a Disposable PEEP Valve). In one embodiment, the Disposable PEEP Valve may be connected to the end of the Corrugated Exhaust Tubing. In another embodiment, the Disposable PEEP Valve may allow for the one-way airflow of waste aerosolized Platelet Rich Plasma/Stem Cell solution and Carbon Dioxide from the Semi-Rebreathing Chamber and the Corrugated Exhaust Tubing.

In one embodiment, the combined Corrugated Exhaust Tubing/Disposable PEEP Valve may be plugged into Intake Port 503. In one embodiment, Intake Port may allow waste aerosolized Platelet Rich Plasma/Stem Cell solution and Carbon Dioxide to pass from the Corrugated Exhaust Tubing through a Disposable HEPA Filter 504. In one embodiment, Disposable HEPA Filter may capture any aerosolized Platelet Rich Plasma/Stem Cell solution particles and may allow only Carbon Dioxide to escape through Exhaust Port 505.

In another embodiment, the Exhaust System may also contain an Ultraviolet Light. In one embodiment, the Ultraviolet Ught may sterilize the escaping exhaust before and/or after it passes through the Disposable HEPA Filter.

Figure 7:
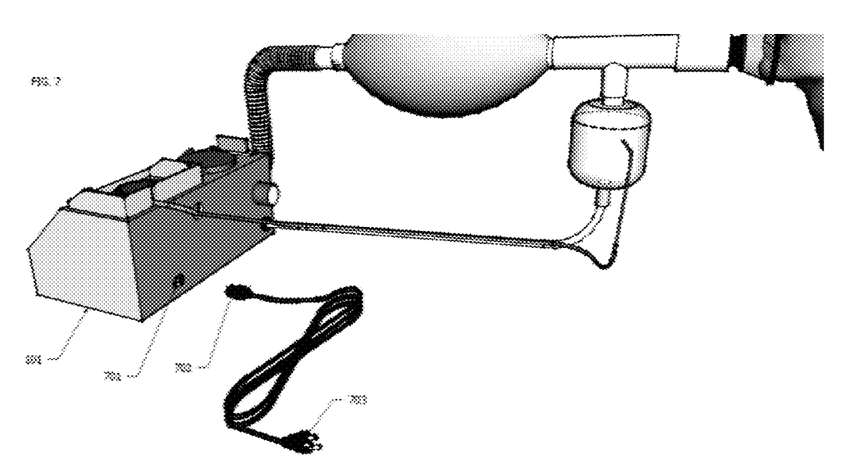
FIG. 7 is a rear-view illustration of a Platelet Rich Plasma/Stem Cell Dispensing System.

| | Element Number | Element Name |
|---|---|---|
| FIG. 7 | 101 | Platelet Rich Plasma/Stem Cell Dispensing System |
| | 701 | AC Plug Port |
| | 702 | AC Plug |
| | 703 | AC Plug Prongs |

FIG. 7 is a rear-view illustration of a Platelet Rich Plasma/Stem Cell Dispensing System 101, according to the embodiment of the present invention. In one embodiment, the Platelet Rich Plasma/Stem Cell Dispensing System may contain an AC Plug Port 701, to run off external power or to charge the internal rechargeable battery. In one embodiment, the user may plug one end of the AC Plug 702, into AC Plug Port. In another embodiment, the user may plug the AC Plug Prongs 703, into an electrical outlet, hereby supplying power to the Platelet Rich Plasma/Stem Cell Dispensing System.

Also utilizing variable energy sources to adapt and comply with local standards for portability and global compatibility.

Figure 8:
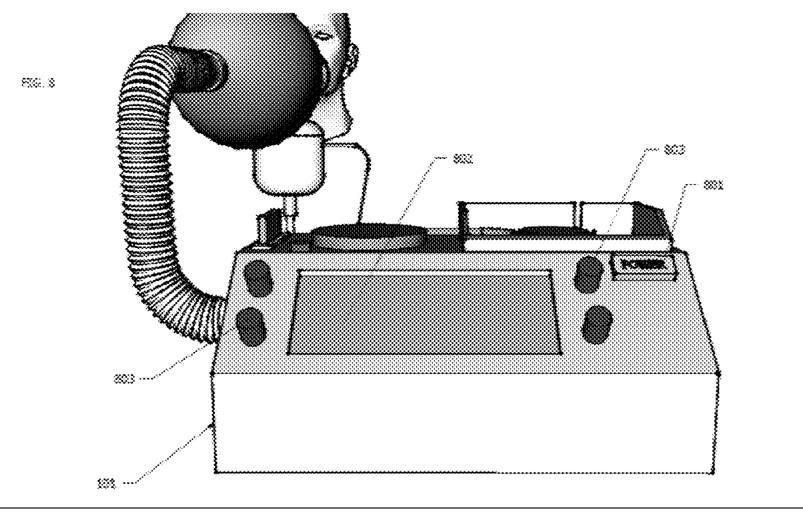
FIG. 8 is a front view illustration of a Platelet Rich Plasma/Stem Cell Dispensing System, detailing the Display and Controls.

| | Element Number | Element Name |
|---|---|---|
| FIG. 8 | 101 | Platelet Rich Plasma/Stem Cell Dispensing System |
| | 801 | Power Button |
| | 802 | Display |
| | 803 | Control Knob(s) |

FIG. 8 is a front view illustration of a Platelet Rich Plasma/Stem Cell Dispensing System 101, detailing the Display and Controls, according to the embodiment of the present invention. In one embodiment, the Platelet Rich Plasma/Stem Cell Dispensing System may contain Power Button 801. In one embodiment, the user may depress Power Button to turn ON the power to the Platelet Rich Plasma/Stem Cell Dispensing System.

In another embodiment, the Platelet Rich Plasma/Stem Cell Dispensing System may also contain Display 802. In one embodiment, the Display may be an LCD, an OLED, an AMOLED or any other type of display technology. In one embodiment, the Display may be backlit to be easily read in low lighting conditions. In one embodiment, information specific to the respiratory treatment (such as oxygen concentration, oxygen flow volume, etc.) may be viewed on the Display. In one embodiment, Display may also be a Touchscreen. In this embodiment, the user may control and/or adjust the respiratory treatment (such as oxygen concentration, oxygen flow volume, etc.) from the Touchscreen.

In another embodiment, Platelet Rich Plasma/Stem Cell Dispensing System may contain Control Knob(s) 803. In one embodiment, Control Knob(s) may be used to control and/or adjust the respiratory treatment (such as oxygen concentration, oxygen flow volume, etc.).

Figure 9:
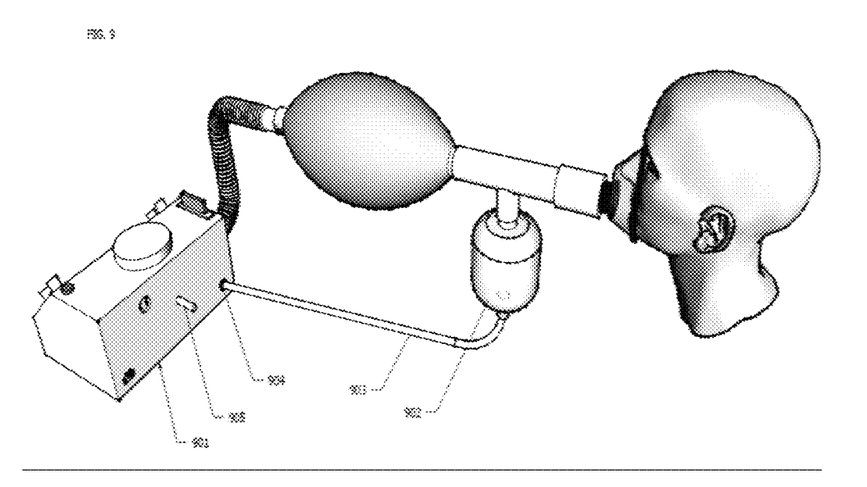
FIG. 9 is a rear-view illustration of a Platelet Rich Plasma/Stem Cell Dispensing System.

| | Element Number | Element Name |
|---|---|---|
| FIG. 9 | 901 | Platelet Rich Plasma/Stem Cell Dispensing System |
| | 902 | Air-Flow Driven Nebulizer |
| | 903 | Nebulizer Oxygen Line |
| | 904 | Oxygen Outflow/Compressor Port |
| | 905 | Oxygen Inflow Port |

FIG. 9 is a rear-view illustration of a Platelet Rich Plasma/Stem Cell Dispensing System 901, according to the embodiment of the present invention. In another embodiment, the Platelet Rich Plasma/Stem Cell Dispensing System may contain all of the embodiments described above. However, in this embodiment, the Platelet Rich Plasma/Stem Cell Dispensing System may not contain an Automatic Centrifuge/PRP Processing System. In this embodiment, the Platelet Rich Plasma/Stem Cells may be first separated from whole blood via a separate centrifugation process in a stand-alone centrifuge.

In another embodiment, the Air-Flow Driven Nebulizer 902, may be opened and may be filled with the Platelet Rich Plasma/Stem Cell solution. In one embodiment, the Air-Flow Driven Nebulizer containing the Platelet Rich Plasma/Stem Cell solution may be closed/sealed and Nebulizer Oxygen Line 903, may be attached to its base.

In another embodiment, the opposite end of the Nebulizer Oxygen Line may be attached the Oxygen Outflow/Compressor Port 904. In this embodiment, oxygen may be supplied to the Air-Flow Driven Nebulizer, which may be used to aerosolize the Platelet Rich Plasma/Stem Cell solution contained therein.

In another embodiment, the Platelet Rich Plasma/Stem Cell Dispensing System may also contain Oxygen Inflow Port 905. In one embodiment, an external oxygen source may be connected to Oxygen Inflow Port. In this manner, oxygen may be supplied to aerosolize the Platelet Rich Plasma/Stem Cell solution contained in the Air-Flow Driven Nebulizer.

In another embodiment, all further embodiments (such as Connector, Face Mask, Semi-Rebreathing Chamber and Exhaust System) described above may remain unchanged.

Figure 10:
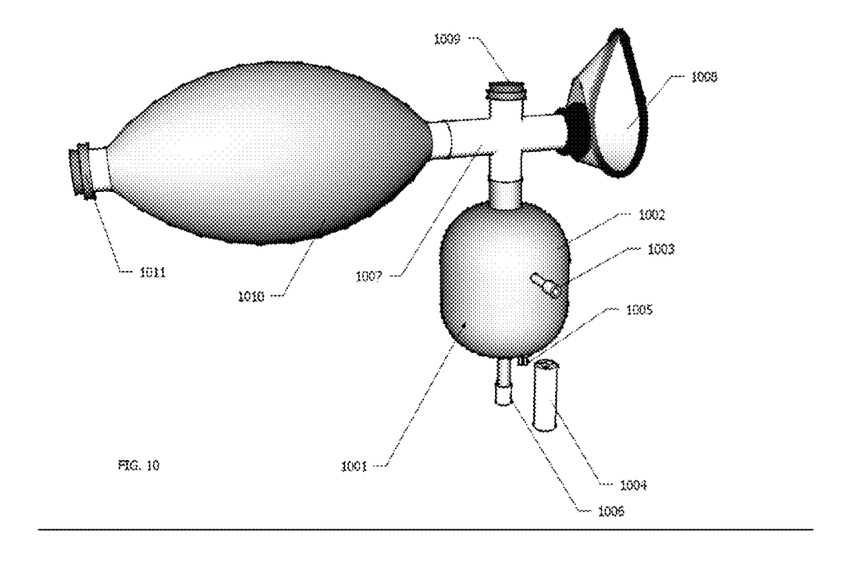
FIG. 10 is an illustration of a Handheld Platelet Rich Plasma/Stem Cell Dispensing System.

| | Element Number | Element Name |
|---|---|---|
| FIG. 10 | 1001 | Handheld Platelet Rich Plasma/Stem Cell Dispensing System |
| | 1002 | Nebulizing Chamber |
| | 1003 | PRP Solution Entry Port |
| | 1004 | Power Source |
| | 1005 | Plug |
| | 1006 | Oxygen Inflow Port |
| | 1007 | T-Connector |
| | 1008 | Face Mask |
| | 1009 | Disposable HEPA Filter |
| | 1010 | Semi-Rebreathing Chamber |

FIG. 10 is an illustration of a Handheld Platelet Rich Plasma/Stem Cell Dispensing System 1001, according to the embodiment of the present invention. In one embodiment, the Handheld Platelet Rich Plasma/Stem Cell Dispensing System may be a more portable version of the Platelet Rich Plasma/Stem Cell Dispensing System.

In one embodiment, the Handheld Platelet Rich Plasma/Stem Cell Dispensing System may contain a Nebulizing Chamber 1002. In one embodiment, Platelet Rich Plasma/Stem Cell solution may be first separated from whole blood via a separate centrifugation process in a stand-alone centrifuge. Platelet Rich Plasma/Stem Cell solution may be inserted via a syringe into the Nebulizing Chamber via PRP Solution Entry Port 1003. In one embodiment, the PRP Solution Entry Port may be a one-way valve which may allow the one-way travel of the Platelet Rich Plasma/Stem Cell solution into the Nebulizing Chamber.

In another embodiment, the Handheld Platelet Rich Plasma/Stem Cell Dispensing System may also contain a Power Source 1004. In one embodiment, the Power Source may be a rechargeable battery pack. In one embodiment, the user may attach the Power Source to Plug 1005. In this manner, power may be supplied to the Nebulizing Chamber to oscillate a piezoelectric element, which may vaporize the Platelet Rich Plasma/Stem Cell solution into an inhalable mist.

In another embodiment, the Power Source may also be used as a control unit for turning the power to the Nebulizing Chamber ON or OFF. In one embodiment, the user may turn the attached Power Source one-quarter turn to the right to turn ON power to the Nebulizing Chamber. In another embodiment, after the Nebulizing Chamber is turned ON, the user may turn the attached Power Source one quarter turn to the left to turn OFF power to the Nebulizing Chamber.

In another embodiment, the user may turn the attached Power Source one quarter turn to the right to turn ON power to the Nebulizing Chamber at ¼ (quarter) speed. In another embodiment, the user may turn the attached Power Source two quarter turns to the right to turn ON power to the Nebulizing Chamber at ½ (one-half) speed. In another embodiment, the user may turn the attached Power Source three quarter turns to the right to turn ON power to the Nebulizing Chamber at ¾ speed. In another embodiment, the user may turn the attached Power Source four three quarter turns to the right to turn ON power to the Nebulizing Chamber at full speed.

In another embodiment, an external oxygen source may be connected to Oxygen Inflow Port 1006. In this manner, oxygen may be supplied to aerosolize the Platelet Rich Plasma/Stem Cell solution contained in the Nebulizing Chamber.

In one embodiment, the Handheld Platelet Rich Plasma/Stem Cell Dispensing System may also contain T-Connector 1007. In one embodiment, the T-Connector may be attached to the top of the Nebulizing Chamber containing the Platelet Rich Plasma/Stem Cell solution. In one embodiment, one end of the T-Connector may be connected to the end of Face Mask 1008. In one embodiment, the Face Mask may be placed over the nose and mouth of the patient receiving respiratory therapy. In this embodiment, the patient may breathe normally to inhale the Platelet Rich Plasma/Stem Cell solution being aerosolized in the Nebulizing Chamber into their respiratory system.

In another embodiment, T-Connector may contain Disposable HEPA Filter 1009. In one embodiment, Disposable HEPA Filter Cap may capture any aerosolized Platelet Rich Plasma/Stem Cell solution particles which the patient may exhale; and may allow only Carbon Dioxide to escape from the Handheld Platelet Rich Plasma/Stem Cell Dispensing System.

In another embodiment, the opposite end of the T-Connector (the end opposite to the Face Mask) may be connected to Semi-Rebreathing Chamber 1010. In one embodiment, any unused portion of the aerosolized Platelet Rich Plasma/Stem Cell solution which is expelled from the patient's respiratory system may become contained within the Semi-Rebreathing Chamber. In this embodiment, the unused portion of the aerosolized Platelet Rich Plasma/Stem Cell solution may be recycled back into the patient's respiratory system.

In another embodiment, a Secondary Disposable HEPA Filter Cap 1011 may be attached to the Semi-Rebreathing Chamber's exhaust port. In one embodiment, the Secondary Disposable HEPA Filter may capture any aerosolized Platelet Rich Plasma/Stem Cell solution particles and may allow only Carbon Dioxide to escape from the Semi-Rebreathing Chamber's exhaust port.

Figure 11:
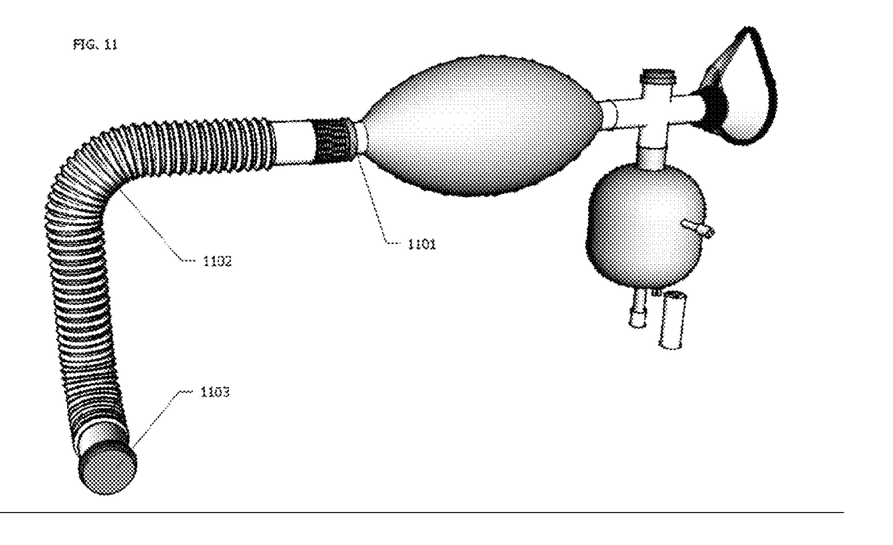
FIG. 11 is an illustration of Handheld Platelet Rich Plasma/Stem Cell Dispensing System, attached to an Exhaust System.

| Element Number | Element Name |
|---|---|
| FIG. 11 | |
| 1001 | Handheld Platelet Rich Plasma/Stem Cell Dispensing System |
| 1009 | Disposable HEPA Filter Cap |
| 1101 | Disposable HEPA Filter Connector |
| 1102 | Corrugated Exhaust Tubing |

FIG. 11 is an illustration of Handheld Platelet Rich Plasma/Stem Cell Dispensing System 1001, attached to an Exhaust System. In another embodiment, the Handheld Platelet Rich Plasma/Stem Cell Dispensing System may contain all of the embodiments described above; however, in this embodiment, the Handheld Platelet Rich Plasma/Stem Cell Dispensing System may be attached to an Exhaust System. In one embodiment, the Semi-Rebreathing Chamber's exhaust port may be fitted with a Disposable HEPA Filter Connector 1101, instead of a Disposable HEPA Filter. In this embodiment, the Disposable HEPA Filter Connector may serve to functions. In one embodiment, the Disposable HEPA Filter Connector may capture any aerosolized Platelet Rich Plasma/Stem Cell solution particles and may allow only Carbon Dioxide to escape from the Semi-Rebreathing Chamber. In another embodiment, the Disposable HEPA Filter Connector may allow Corrugated Exhaust Tubing 1102, to be attached to the Handheld Platelet Rich Plasma/Stem Cell Dispensing System. In one embodiment, Corrugated Exhaust Tubing may remove any waste, aerosolized Platelet Rich Plasma/Stem Cell solution (which is not recycled into the patient's respiratory system at the Semi-Rebreathing Chamber stage); and any Carbon Dioxide which the patient expels.

In another embodiment, Corrugated Exhaust Tubing may be capped off with a Disposable HEPA Filter 1009. In one embodiment, Disposable HEPA Filter Cap may capture any aerosolized Platelet Rich Plasma/Stem Cell solution particles which the patient may exhale; and may allow only Carbon Dioxide to escape from the Handheld Platelet Rich Plasma/Stem Cell Dispensing System.

Figure 12:
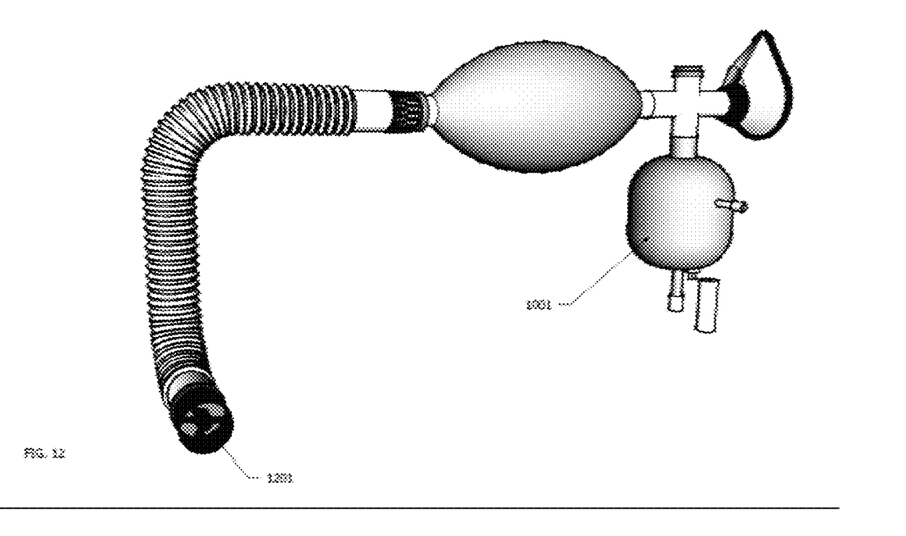
FIG. 12 is an illustration of Handheld Platelet Rich Plasma/Stem Cell Dispensing System, attached to an Socket 303, on the Platelet Rich Plasma/Stem Cell Dispensing System. In this embodiment, power may be supplied to the Ultrasonic Nebulizer to oscillate a piezoelectric element, which may vaporize the Platelet Rich Plasma/Stem Cell solution into an inhalable mist.

| Element Number | Element Name |
|---|---|
| FIG. 12 | |
| 1001 | Handheld Platelet Rich Plasma/Stem Cell Dispensing System |
| 1201 | Exhaust Impeller |

FIG. 12 is an illustration of Handheld Platelet Rich Plasma/Stem Cell Dispensing System 1001, attached to an Exhaust System and containing an Exhaust Impeller Fan. In one embodiment, the Handheld Platelet Rich Plasma/Stem Cell Dispensing System may contain all of the embodiments described above in FIG. 11, however, in this embodiment; the Handheld Platelet Rich Plasma/Stem Cell Dispensing System may also contain Exhaust Impeller 1201.

In one embodiment, the Exhaust Impeller may spin at a high speed and may create a vortex, which may remove any aerosolized Platelet Rich Plasma/Stem Cell solution particles which the patient may exhale from the Corrugated Exhaust Tubing.

Figure 13:
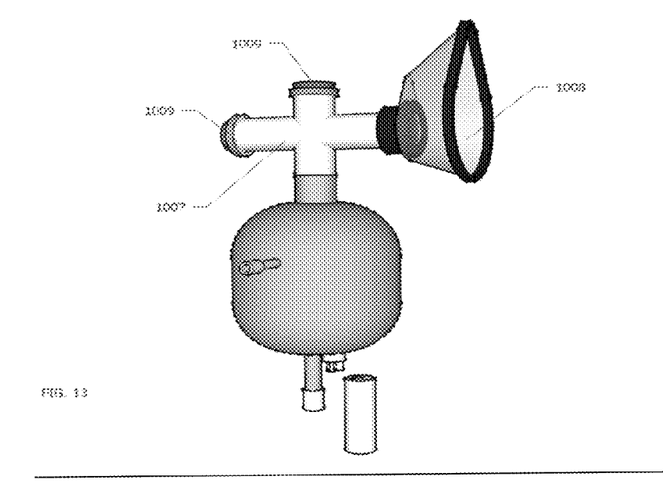

| Element Number | Element Name |
|---|---|
| FIG. 13 | |
| 1001 | Handheld Platelet Rich Plasma/Stem Cell Dispensing System |
| 1007 | T-Connector |
| 1008 | Face Mask |
| 1009 | Disposable HEPA Filter |

FIG. 13 is an illustration of Handheld Platelet Rich Plasma/Stem Cell Dispensing System 1001, without a Semi-Rebreathing Chamber or an attached Exhaust System. In another embodiment, the Handheld Platelet Rich Plasma/Stem Cell Dispensing System may contain all of the embodiments described above; however, in this embodiment, the Handheld Platelet Rich Plasma/Stem Cell Dispensing System may not contain a Semi-Rebreathing Chamber or an attached Exhaust System.

In one embodiment, the T-Connector 1007 may be attached to the top of the Nebulizing Chamber containing the Platelet Rich Plasma/Stem Cell solution. In one embodiment, one end of the T-Connector may be connected to the end of Face Mask 1008. In one embodiment, the Face Mask may be placed over the nose and mouth of the patient receiving respiratory therapy.

In this embodiment, the patient may breathe normally to inhale the Platelet Rich Plasma/Stem Cell solution being aerosolized in the Nebulizing Chamber into their respiratory system.

In another embodiment, T-Connector may contain Disposable HEPA Filter Cap 1009. In one embodiment, Disposable HEPA Filter Cap(s) may capture any aerosolized Platelet Rich Plasma/Stem Cell solution particles, which the patient may exhale; and may allow only Carbon Dioxide to escape from the Handheld Platelet Rich Plasma/Stem Cell Dispensing System.

Figure 14:
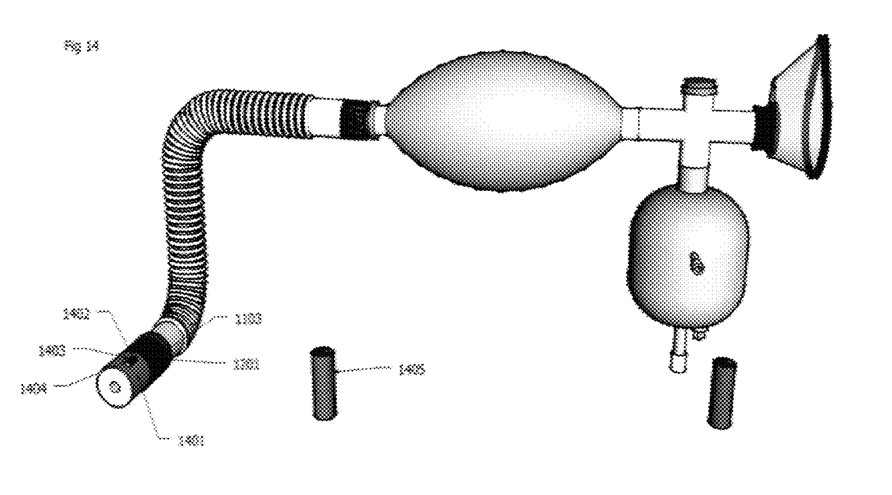

| Element Number | Element Name |
|---|---|
| FIG. 14 | |
| 1001 | Handheld Platelet Rich Plasma/Stem Cell Dispensing System |
| 1401 | Sterilizing Heater Module |
| 1402 | Light Indicates Low Temperature, Less than 392° Deg Fahrenheit |
| 1403 | Light Indicates Temperature Equal to 392° Deg Fahrenheit or Greater |
| 1404 | Light Indicates Low Power, Power source needs to be replaced |
| 1405 | Rechargeable Power Source used to Power Fan and/or Heater module |

FIG. 14 is an illustration of a Handheld Platelet Rich Plasma/Stem Cell Dispensing System 1001, containing a Sterilization Module. In another embodiment, the Handheld Platelet Rich Plasma/Stem Cell Dispensing System may contain all of the embodiments described above; however, in this embodiment, the Handheld Platelet Rich Plasma/Stem Cell Dispensing System may contain a Sterilizing Heater Module 1401. In one embodiment, Exhaust Impeller may force any captured aerosolized Platelet Rich Plasma/Stem Cell solution particles from the Corrugated Exhaust Tubing through Sterilizing Heater Module. In this manner any active biological materials or particles may be sterilized or neutralized before exiting the system. Indicator lights 1402, 1403 and 1404 provide a means to tell the operator when the unit is safe to use.

What is claimed is:

1. A platelet rich plasma (PRP) and stem cell dispensing system comprising:
   an automatic centrifuge/PRP processor creating a PRP/stem cell solution harvested from whole blood of a host;
   a nebulizer connected to the automatic centrifuge/PRP processor vaporizing the PRP/stem cell solution with oxygen, said nebulizer including a T-connector tube connecting the nebulizer and a breathing mask;
   a semi-rebreathing chamber also connected to the connector tube at one end of the semi-rebreathing chamber; and
   an exhaust tube connected to the semi-rebreathing chamber at an end opposite from the one end;
   wherein the system is adapted to be used such that a patient using the breathing mask first inhales vaporized PRP/stem cell vapor from the nebulizer, and exhales an unused portion of the inhaled vapor into the semi-rebreathing chamber, the exhaled portion available to be inhaled again.

2. The platelet rich plasma (PRP) and stem cell dispensing system of claim 1 further comprising an exhaust fan associated with the exhaust tube, the exhaust fan aiding in exhausting vapor and gasses through an exhaust port.

3. The platelet rich plasma (PRP) and stem cell dispensing system of claim 2 further comprising a a high efficiency particulate air (HEPA) filter at the exhaust port, filtering out vapor particles, allowing only gasses to pass.

4. The platelet rich plasma (PRP) and stem cell dispensing system of claim 3 further comprising an ultraviolet light source sterilizing biological matter in the exhaust gases either before or after the HEPA filter.

* * * * *